(12) United States Patent
Wilfley et al.

(10) Patent No.: US 8,160,690 B2
(45) Date of Patent: Apr. 17, 2012

(54) SYSTEM AND METHOD FOR DETERMINING ELECTRODE-TISSUE CONTACT BASED ON AMPLITUDE MODULATION OF SENSED SIGNAL

(75) Inventors: Brian P. Wilfley, Los Altos, CA (US); Joseph A. Heanue, Los Altos, CA (US); Stuart L. Friedman, Palo Alto, CA (US)

(73) Assignee: Hansen Medical, Inc., Mountain View, CA (US)

( * ) Notice: Subject to any disclaimer, the term of this patent is extended or adjusted under 35 U.S.C. 154(b) by 355 days.

(21) Appl. No.: 11/762,778

(22) Filed: Jun. 14, 2007

(65) Prior Publication Data

US 2008/0312713 A1    Dec. 18, 2008

(51) Int. Cl.
*A61B 5/05* (2006.01)
(52) U.S. Cl. .......................... 600/547; 607/28
(58) Field of Classification Search .............. 607/28
See application file for complete search history.

(56) References Cited

U.S. PATENT DOCUMENTS

| | | | |
|---|---|---|---|
| 5,074,303 A * | 12/1991 | Hauck | 607/17 |
| 5,282,840 A * | 2/1994 | Hudrlik | 607/28 |
| 5,341,807 A * | 8/1994 | Nardella | 600/381 |
| 5,383,874 A | 1/1995 | Jackson et al. | |
| 5,447,529 A | 9/1995 | Marchlinski et al. | |
| 5,454,377 A | 10/1995 | Dzwonczyk et al. | |
| 5,485,849 A | 1/1996 | Panescu et al. | |
| 5,494,042 A | 2/1996 | Panescu et al. | |
| 5,759,159 A | 6/1998 | Masreliez | |
| 5,833,621 A | 11/1998 | Panescu et al. | |
| 6,101,409 A | 8/2000 | Swanson et al. | |
| 6,391,024 B1 * | 5/2002 | Sun et al. | 606/34 |
| 6,423,057 B1 | 7/2002 | He et al. | |
| 6,726,675 B1 | 4/2004 | Beyar | |
| 7,090,683 B2 | 8/2006 | Brock et al. | |
| 2006/0084945 A1 | 4/2006 | Moll et al. | |
| 2007/0060833 A1 * | 3/2007 | Hauck | 600/547 |
| 2007/0185485 A1 | 8/2007 | Hauck et al. | |
| 2008/0275465 A1 | 11/2008 | Paul et al. | |
| 2008/0312521 A1 | 12/2008 | Solomon | |

FOREIGN PATENT DOCUMENTS

WO    WO 2008/157399    12/2008

OTHER PUBLICATIONS

PCT International Search Report and Written Opinion for PCT/US2008/066979 of the International Searching Authority, Applicant Hansen Medical, Inc., dated Oct. 24, 2008, Forms PCT/ISA/210, 220 and 237 (13 pages).
PCT Patent Application No. PCT/US2008/066979 filed Jun. 13, 2008 in the name of Wilfley et al., International Preliminary Report on Patentability mailed Dec. 30, 2009.
U.S. Appl. No. 11/702,779, filed Jun. 14, 2007 in the name of Solomon. Non-final Office Action mailed Aug. 10, 2010.
U.S. Appl. No. 11/762,779, filed Jun. 14, 2007 in the name of Solomon, Final Office Action mailed Apr. 25, 2011.

* cited by examiner

*Primary Examiner* — Carl H Layno
*Assistant Examiner* — Jeremiah Kimball
(74) *Attorney, Agent, or Firm* — Levine Bagade Han LLP (57) ABSTRACT

Methods and systems for monitoring contact between a medical probe and tissue are provided. A medical probe is introduced into a patient adjacent the tissue. An electrical parameter, e.g., electrical admittance, is measured between a first electrode located on the medical probe and a second electrode remote from the first electrode. The electrical parameter is amplitude modulated in response to a physiological cycle of the patient. Contact between the medical probe and the tissue is detected based on the amplitude modulation of the measured electrical parameter.

23 Claims, 6 Drawing Sheets

SYSTEM AND METHOD FOR DETERMINING ELECTRODE-TISSUE CONTACT BASED ON AMPLITUDE MODULATION OF SENSED SIGNAL

CROSS REFERENCE TO RELATED APPLICATION

This application is related to U.S. patent application Ser. No. 11/762,779, filed on the same date herewith. The disclosure of this application is expressly incorporated herein by reference.

FIELD OF THE INVENTION

The present inventions generally relate to medical probes or instruments, and more particularly to systems and methods for determining contact between a medical probe or instrument and tissue.

BACKGROUND OF THE INVENTION

In many procedures, such as minimally-invasive surgery or catheter-based diagnosis and/or intervention, it is important for the physician to know the location of an instrument or probe, such as a diagnostic and/or therapeutic catheter, probe, arm, or other structure relative to the patient's internal anatomy. During cardiovascular catheterization procedures to address electrophysiologic problems, for example, a physician may steer an electrophysiology mapping catheter, typically under fluoroscopy, through a main vein or artery into the interior region of the heart that is to be treated. The physician then may determine the source of the cardiac rhythm disturbance (i.e., the targeted heart tissue) either strictly by anatomical considerations or by placing mapping elements carried by the catheter into contact with the heart tissue, and operating the mapping catheter to generate an electrophysiology map of the interior region of the heart. Having identified the targeted heart tissue, the physician then steers a radio frequency (RF) ablation catheter (which may or may not be the same catheter as the mapping catheter above) into the heart and places an ablation electrode in the blood stream against the targeted heart tissue carried by the catheter tip near the targeted heart tissue, and directs RF energy from the ablating element to ablate the tissue and form a lesion, thereby treating the cardiac disturbance. It is important that the contact between the electrode and the tissue be maximized to direct the RF energy toward the targeted heart tissue rather than through the blood stream.

It is known that the impedance between an electrode and tissue increases with an increase in contact between the electrode and the tissue. Based on this principle, prior art methods have taken impedance measurements from the electrode to ascertain when sufficient contact is established between the electrode and the targeted heart tissue for carrying out the ablation procedure. A baseline impedance measurement can be taken when the electrode is known to reside entirely within the blood stream, and contact with tissue is assumed to have occurred when the impedance has increased by a predetermined amount set empirically for a given system.

Besides ascertaining electrode-tissue contact for purposes of effecting sufficient tissue ablation or other diagnosis and/or intervention, it is sometimes desirable to determine the forces applied at the interfaces between electrodes and tissue structures, or the amount of electrode surface in contact with the tissue, to prevent or minimize the chance that the tissue will be inadvertently damaged or punctured by the interventional and/or diagnostic tools carrying the electrodes. While a physician can typically obtain some level of tactile feel for the force created between the instrument and tissue structures during manual manipulations of relatively light-weight instruments such as catheters within the patient, optimal resolution of the sensation maybe inadequate, and with larger instruments, manual sensation of distally-applied forces may be substantially impractical or impossible. Robotic systems that automatically manipulate catheters in response to movements of a control device at a remote user interface have recently been developed. Such systems are operated without direct manual manipulation of the instruments, and thus a physician cannot rely on directly-transmitted tactile feedback, but instead, may rely upon feedback provided by the robotic system, such as visual, audible, and/or tactile feedback, to maintain precision control over the subject instrument or instruments. It is preferred that such robotic systems be enabled with multiple means for determining the extent of contact or force between instrument electrodes and tissue.

Although the acquisition of impedance measurements has been generally successful in determining when an electrode has been placed in contact with tissue, the variation in impedance of tissue and blood between patients makes it difficult to accurately determine the extent of such electrode-tissue contact. Thus, during tissue ablation and other diagnostic and/or interventional procedures, firm effective contact between the electrode and tissue, as opposed to insufficient contact between the electrode and tissue, may not always be ascertained. With respect to preventing inadvertent damage to tissue, normal electrode-tissue contact, as opposed to contact that risks damage to tissue, may not always be ascertained.

There thus remains a need for an improved system and method for ascertaining contact between an electrode and tissue for various configurations of diagnostic and/or interventional instruments in various clinical settings.

SUMMARY OF THE INVENTION

In accordance with a first aspect of the present inventions, a method of monitoring contact between a medical probe (e.g., an intravascular catheter) and tissue (e.g., heart tissue) is provided. The method comprises introducing the medical probe into a patient (e.g., within a heart chamber) adjacent the tissue, and measuring an electrical parameter (e.g., an electrical admittance) between a first electrode of the medical probe and a second electrode remote from the first electrode, wherein the electrical parameter is amplitude modulated by a physiological cycle of the patient (e.g., a respiratory cycle or heart cycle). By way of non-limiting example, the first electrode may be a tip electrode, and the second electrode may be a ground patch electrode attached to the skin of the patient or another electrode of the medical probe. One method comprises transmitting a time varying signal between the first electrode and the second electrode, and detecting the time varying signal, wherein the electrical parameter measurement is based on the detection of the time varying signal.

The method further comprises detecting contact between the medical probe (e.g., the first electrode) and the tissue based on the amplitude modulation of the measured electrical parameter. By way of non-limiting example, the contact detection may comprise comparing a magnitude of the amplitude modulation to a threshold, and determining that the medical probe is in contact with the tissue if the magnitude of the amplitude modulation exceeds the threshold. In an optional method, the contact detection comprises determining an extent of the contact based on a magnitude of the amplitude modulation. Another optional method comprises performing a medical procedure on the tissue when the contact between the medical probe and the tissue has been detected.

In accordance with a second aspect of the present inventions, a medical system comprises a medical probe (e.g., an intravascular catheter) having a probe shaft and a first electrode (e.g., a tip electrode) carried by the probe shaft. The medical system further comprises a second electrode; for example, a ground patch electrode configured for being attached to the skin of the patient or another electrode carried by the probe shaft. The system further comprises a monitoring device configured for measuring an electrical parameter (e.g., an electrical admittance) between the first electrode and the second electrode, wherein the electrical parameter is amplitude modulated by a physiological cycle of the patient (e.g., a respiratory cycle or heart cycle). By way of non-limiting example, the monitoring device may be configured for transmitting a time varying signal between the first electrode and the second electrode, and detecting the time varying signal, wherein the electrical parameter measurement is based on the detection of the time varying signal.

The monitoring device is configured for conveying an output to a user indicative of contact between the medical probe (e.g., the first electrode) and the tissue, the output being based on the amplitude modulation of the measured electrical parameter. By way of non-limiting example, the monitoring device may be configured for comparing a magnitude of the amplitude modulation to a threshold, and determining that the medical probe is in contact with the tissue if the magnitude of the amplitude modulation exceeds the threshold. In another embodiment, the output is a visual display of the amplitude modulation of the measured electrical parameter. In an optional embodiment, the monitoring device is configured for determining an extent of the contact based on a magnitude of the amplitude modulation. The system may comprise a radio frequency (RF) generator configured for delivering ablation energy to the first electrode.

In accordance with a third aspect of the present inventions, a tissue contact monitoring device is provided. The monitoring device comprises an electrical terminal configured for coupling to a medical probe having a first electrode, and a processor configured for measuring an electrical parameter (e.g., an electrical admittance) between the first electrode and a second electrode, wherein the electrical parameter is amplitude modulated by a physiological cycle of the patient (e.g., a respiratory cycle or heart cycle). By way of non-limiting example, the monitoring device may comprise a signal generator configured for transmitting a time varying signal between the first electrode and the second electrode, and a signal detector configured for detecting the time varying signal, wherein the processor is configured for measuring the electrical parameter based on the detected time varying signal.

The monitor further comprises a user interface configured for conveying an output indicative of contact between the medical probe and the tissue, the output being based on the amplitude modulation of the measured electrical parameter. By way of non-limiting example, the processor may be configured for comparing a magnitude of the amplitude modulation to a threshold, and determining that the medical probe is in contact with the tissue if the magnitude of the amplitude modulation exceeds the threshold. In another embodiment, the user interface comprises a video monitor and the output is a visual display of the amplitude modulation of the measured electrical parameter. In an optional embodiment, the monitoring device is configured for determining an extent of the contact based on a magnitude of the amplitude modulation.

Other objects and features of the present invention will become apparent from consideration of the following description taken in conjunction with the accompanying drawings.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE
ILLUSTRATED EMBODIMENTS

Figure 1:
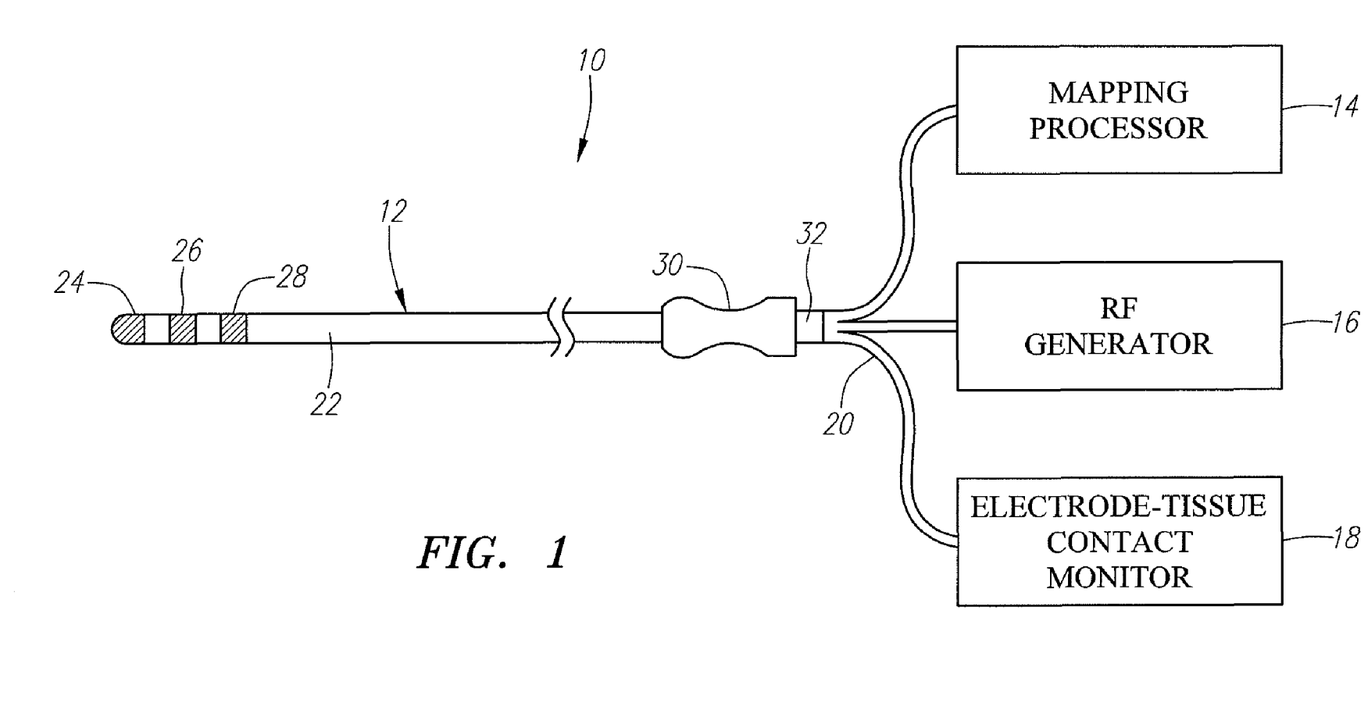
FIG. 1 is a functional block diagram of one embodiment of an electrophysiology (EP) system constructed in accordance with the present inventions.

Referring to FIG. 1, an exemplary electrophysiology (EP) system 10 constructed in accordance with the present inventions is shown. The EP system 10 is particularly suited for mapping a heart by identifying a target tissue site or sites, e.g., aberrant conductive pathways, and for treating the heart by ablating the target tissue site(s). Nevertheless, it should be noted that the concepts disclosed herein may be applied to any process requiring the introduction of a medical probe within a patient's body to diagnose or treat other internal anatomical structures, e.g., the prostrate, brain, gall bladder, uterus, esophagus and other regions in the body.

The EP system 10 generally comprises a mapping/ablation catheter 12, and a mapping processor 14, a radio frequency (RF) generator 16, and an electrode-tissue contact monitor 18 functionally coupled to the mapping/ablation catheter 12 via a cable assembly 20. The mapping/ablation catheter 12 may optionally be mechanically manipulated by a robotic system (not shown). Exemplary robotic systems that can be used to mechanically manipulate the catheter 12 are described in U.S. Pat. No. 7,090,683 and U.S. Patent Publication No. 2006/0084945, which are expressly incorporated herein by reference. It should be noted that the mapping processor 14, RF generator 16, and electrode-tissue contact monitor 18 are functional in nature, and thus, their illustration in FIG. 1 is not meant to limit the structure that performs these functions in any manner. For example, any combination of the mapping processor 14, RF generator 16, and electrode-tissue contact monitor 18 may be embodied in a single device, or each of the mapping processor 14, RF generator 16, or electrode-tissue contact monitor 18 may be embodied in several devices. Also, the functions of these elements can be performed in hardware, software, firmware, or any combination thereof.

The mapping/ablation catheter 12 comprises an elongate catheter member 22, a plurality of electrodes 24, 26, 28 (in this case, three) carried at the distal end of the catheter member 22, and a handle 30 carried at the proximal end of the catheter member 22. All three electrodes 24, 26, 28 on the catheter member 22 are configured to detect electrical signals in the myocardial tissue for subsequent identification of target sites. The distal-most electrode 24 takes the form of a cap electrode disposed at the distal tip 28 of the catheter member 22, and is configured to be used as an ablation electrode to provide ablation energy to the targeted sites when placed adjacent thereto and operated. The electrodes 24, 26 proximal to the electrode 24 take the form of ring electrodes disposed about the catheter member 22 in a suitable manner. The handle 30 includes an electrical connector 32 for electrical coupling to the mapping processor 14, RF generator 16, and electrode-tissue contact processor 18 via the cable assembly 20.

Referring back to FIG. 1, the mapping processor 14 is configured to derive activation times and voltage distribution from the electrical signals obtained from the electrodes (both the tip electrode 24 and the more proximally located ring electrodes 26, 28) to determine irregular electrical signals within the heart, which can then be graphically displayed as a map. Mapping of tissue within the heart is well known in the art, and thus for purposes of brevity, the mapping processor 14 will not be described in further detail. Further details regarding electrophysiology mapping are provided in U.S. Pat. Nos. 5,485,849, 5,494,042, 5,833,621, and 6,101,409, which are expressly incorporated herein by reference.

The RF generator 16 is configured to deliver ablation energy to the ablation electrode (i.e., the tip electrode 24) in a controlled manner in order to ablate sites identified by the mapping processor 14. Alternatively, other types of ablative sources besides the RF generator 16 can be used, e.g., a microwave generator, an acoustic generator, a cryoablation generator, and a laser or other optical generator. Ablation of tissue within the heart is well known in the art, and thus for purposes of brevity, the RF generator 16 will not be described in further detail. Further details regarding RF generators are provided in U.S. Pat. No. 5,383,874, which is expressly incorporated herein by reference.

In the illustrated embodiment, the RF current is delivered to the tip electrode 24 in a monopolar fashion, which means that current will pass from the tip electrode 24, which is configured to concentrate the energy flux in order to have an injurious effect on the surrounding tissue, and a dispersive ground patch electrode (not shown), which is located remotely from the tip electrode 24 and has a sufficiently large area (typically 130 cm$^2$ for an adult), so that the current density is low and non-injurious to surrounding tissue. In the illustrated embodiment, the dispersive electrode may be attached externally to the patient, e.g., using a contact pad placed on the patient's flank. Alternatively, the RF current is delivered to the tip electrode 24 in a multipolar (e.g., bipolar) fashion, which means that current will pass between the tip electrode 24 and one or both of the ring electrodes 26, thereby concentrating the energy flux in order to have an injurious effect on the tissue between the tip electrode 24 and ring electrodes 26, 28.

It should be noted that other types of mapping/ablation catheters can be used in the EP system 10. For example, a catheter having a basket structure of resilient splines, each of which carries a plurality of dedicated mapping electrodes can be used. This catheter may be placed in a heart chamber, so that the resilient splines conform to the endocardial surface of the heart, thereby placing and distributing the mapping electrodes along the entire endocardial surface of the cavity for efficient mapping. The catheter may also have a roving ablation electrode that can be steered in contact with the ablation sites identified by the mapping electrodes. Or a separate ablation catheter with a dedicated ablation electrode or electrodes can be used.

The electrode-tissue contact monitor 18 measures an electrical parameter, and in particular electrical admittance, between the tip electrode 24 and the ground patch electrode (not shown) to detect both the occurrence and extent of catheter contact with heart tissue. Alternatively, the monitor 18 may measure the electrical admittance between the tip electrode 24 and one or both of the ring electrodes 26, 28. Significantly, the electrical admittance measured by the monitor 18 is amplitude modulated by a physiological cycle of the patient in which the mapping/ablation catheter 12 is introduced. The monitor 18 can detect both the occurrence and extent to which the tip electrode 24 contacts heart tissue based on this amplitude modulation.

Referring to FIGS. 2 and 3A-3D, it has been demonstrated that the occurrence and extent to which an electrode contacts heart tissue can be based on the an electrical admittance measured between the electrode and another electrode, and in particular, an amplitude modulation of the electrical admittance caused by a physiological cycle (e.g., a heart cycle or a respiratory cycle).

Figure 2:
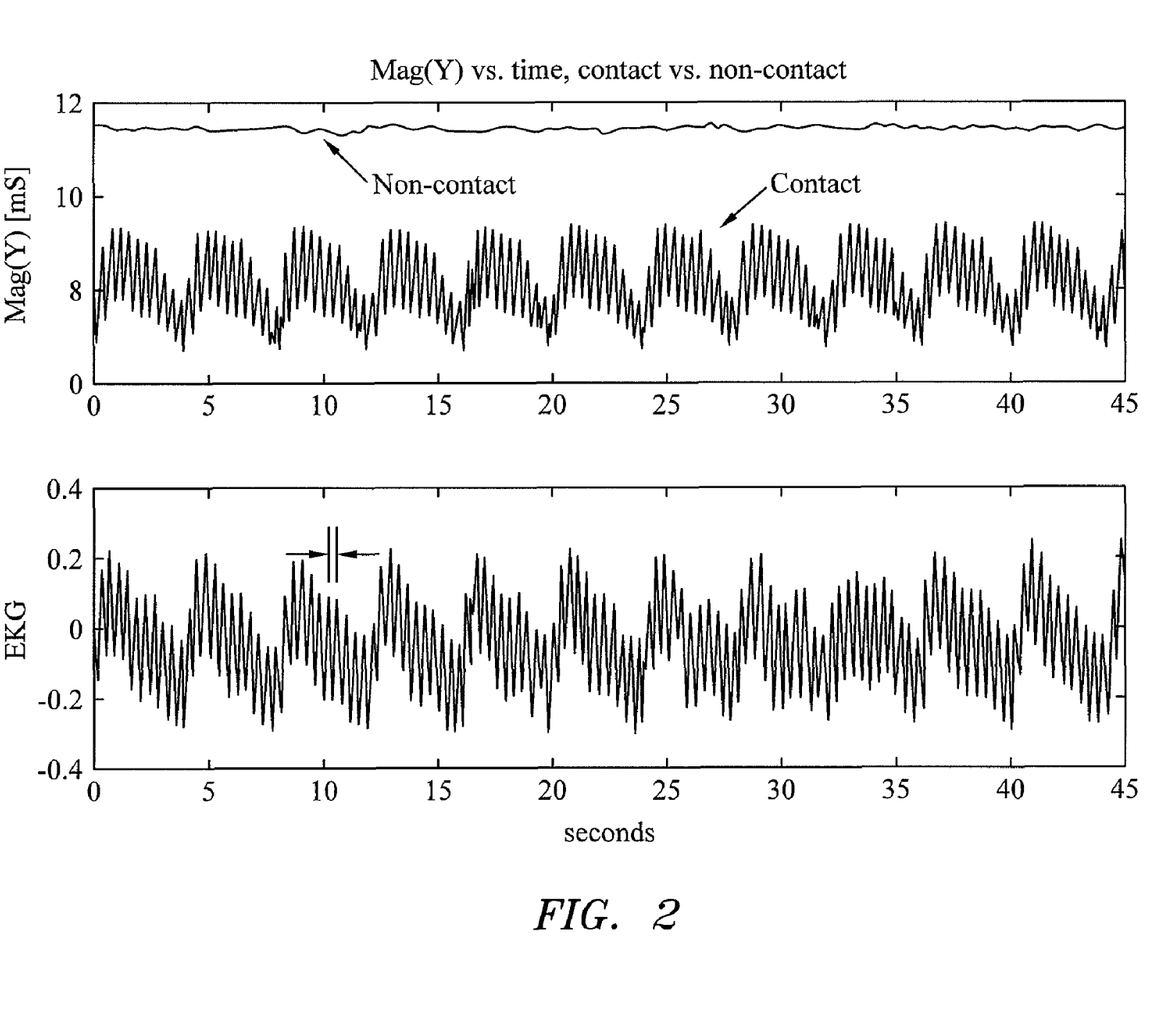
FIG. 2 is a plot illustrating a measured electrical admittance of tissue, as amplitude modulated over time by a cardiac and respiratory cycle.
Figure 3A:
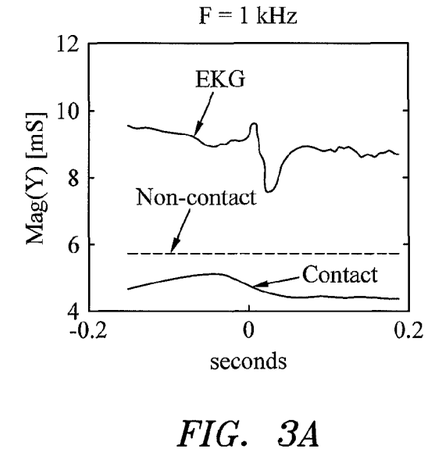
FIGS. 3A-3D are plots illustrating the amplitude modulation of a measured electrical admittance over a single heart beat at various frequencies.
Figure 3B:
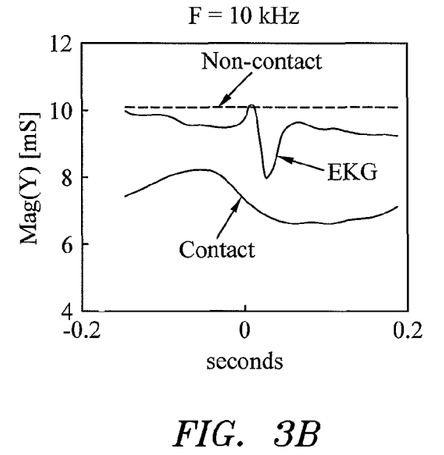
Figure 3C:
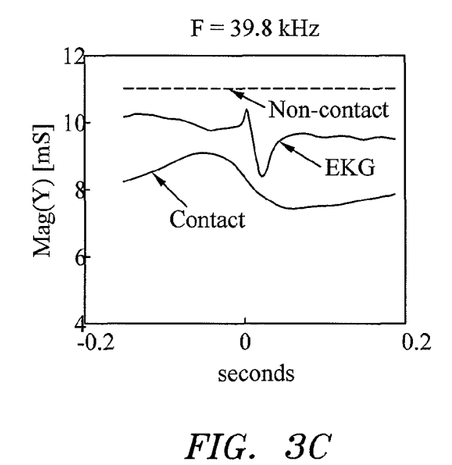
Figure 3D:
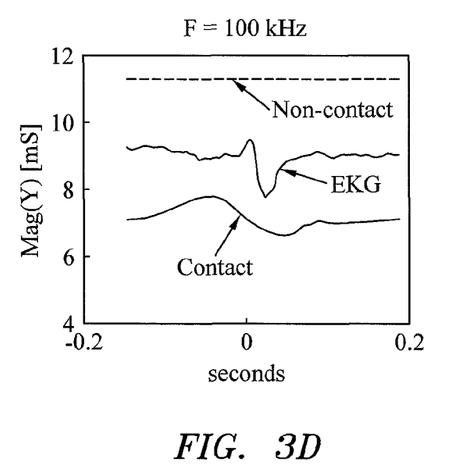

With particular reference to FIG. 2, an electrical admittance measured within the heart of a pig is shown amplitude modulated (shown by the curves in upper graph) by both the heart cycle and the respiratory cycle (shown by the electrocardiogram (EKG) of lower graph). In generating the graphs in FIG. 3, a tissue ablation electrode was placed within the atrium of a live pig and a ground patch electrode was placed on the skin of the pig. The admittance between the electrodes were then measured, while the ablation electrode was not placed in contact with the heart tissue (i.e., fully immersed in the blood pool) placed in contact with the blood pool, and while the ablation electrode was placed in contact with the heart tissue, as confirmed via fluoroscopy.

As shown, the measured electrical admittance when the ablation electrode is not in contact with the heart tissue (top curve in upper graph) has a baseline level (approximately, 11.5 mS) that is higher than the baseline level (approximately, 8 mS) of the measured admittance when the ablation electrode is in contact with the heart tissue (bottom curve in upper graph). When the ablation electrode is not in contact with the heart tissue (top curve in upper graph), the magnitude that the measured admittance is amplitude modulated by the heart and respiratory cycles relative to the baseline is relatively small (approximately 0.1 mS). In contrast, when the ablation electrode is in contact with the heart tissue (bottom curve in upper graph), the magnitude that the measured admittance is amplitude modulated by the heart and respiratory cycles relative to the baseline is relatively large (approximately 2.5 mS).

It can be appreciated that the magnitude of the amplitude modulation increases with an increase in contact between the ablation electrode and heart tissue. The presence of amplitude modulation of the admittance measurement is a reliable indicator of whether an electrode is in or is not in contact with heart tissue, and the magnitude of the amplitude modulation of the admittance measurement is a reliable indicator of the quality of contact between the electrode and heart tissue. As shown in FIG. 2, the measured admittance has both a slow modulation (envelope of waveform) that tracks the respiratory cycle of the pig, and a fast modulation that tracks the heart cycle of the pig. Thus, the occurrence and extent of contact between an electrode and heart tissue may be determined based on the amplitude modulation caused by either or both of the respiratory cycle and cardiac cycle.

As previously discussed, the impedance, and thus the baseline levels of the measured admittance, will vary among patients. If only the baseline level of the admittance is measured, variations in the conductance of patient's heart tissue or blood would need to be calibrated out. Significantly, however, the magnitude of the amplitude modulation of a measured admittance, does not vary among patients. Thus, if the amplitude of the amplitude modulation is measured, variations in the conductance of patient's heart tissue or blood would not need to be calibrated out using a separate technique.

Referring now to FIGS. 3A-3D, the magnitude of the admittance is shown for a single heartbeat over four difference frequencies. In each case, the magnitude of the measured admittance when the ablation electrode is not in contact with the heart tissue (dashed curve) is less than the magnitude of the measured admittance when the ablation electrode is in contact with the heart tissue (dotted curve). Also, the measured non-contact admittance remains relatively uniform in response to the single heart beat (solid EKG curve), whereas the measured contact admittance markedly increases in response to the single heart beat. For example, at a frequency of 1 KHz (FIG. 3A), the measured non-contact admittance remains at approximately 5.8 mS, whereas the measured contact admittance increases from approximately 4.5 mS to approximately 5 mS. At a frequency of 10 KHz (FIG. 3B), the measured non-contact admittance remains at approximately 10 mS, whereas the measured contact admittance increases from approximately 7.5 mS to approximately 8.2 mS. At a frequency of 39.8 KHz (FIG. 3C), the measured non-contact admittance remains at approximately 11 mS, whereas the measured contact admittance increases from approximately 8.2 mS to approximately 9.0 mS. At a frequency of 100 KHz (FIG. 3D), the measured non-contact admittance remains at approximately 11.5 mS, whereas the measured contact admittance increases from approximately 7.0 mS to approximately 8.0 mS.

Notably, FIGS. 3A-3D illustrate the modulation of the measured contact admittance as occurring prior to the EKG reading, reflecting the fact that the admittance measurement is being performed in the atrium, while the EKG is measured within the ventricle. In fact, the modulation of the measured contact admittance will be temporally coincident with the depolarization of the atrial heart tissue. It is apparent from FIGS. 3A-3D that the noise is very low, and thus, the signal-to-noise ratio is very high, thereby providing admittance measurements that very accurately represent true electrode-tissue contact and are very sensitive to electrode-tissue contact changes. Also, the frequency range that produces clear admittance measurements is within the safe frequency range during normal operation of approximately 50-100 KHz.

Figure 4:
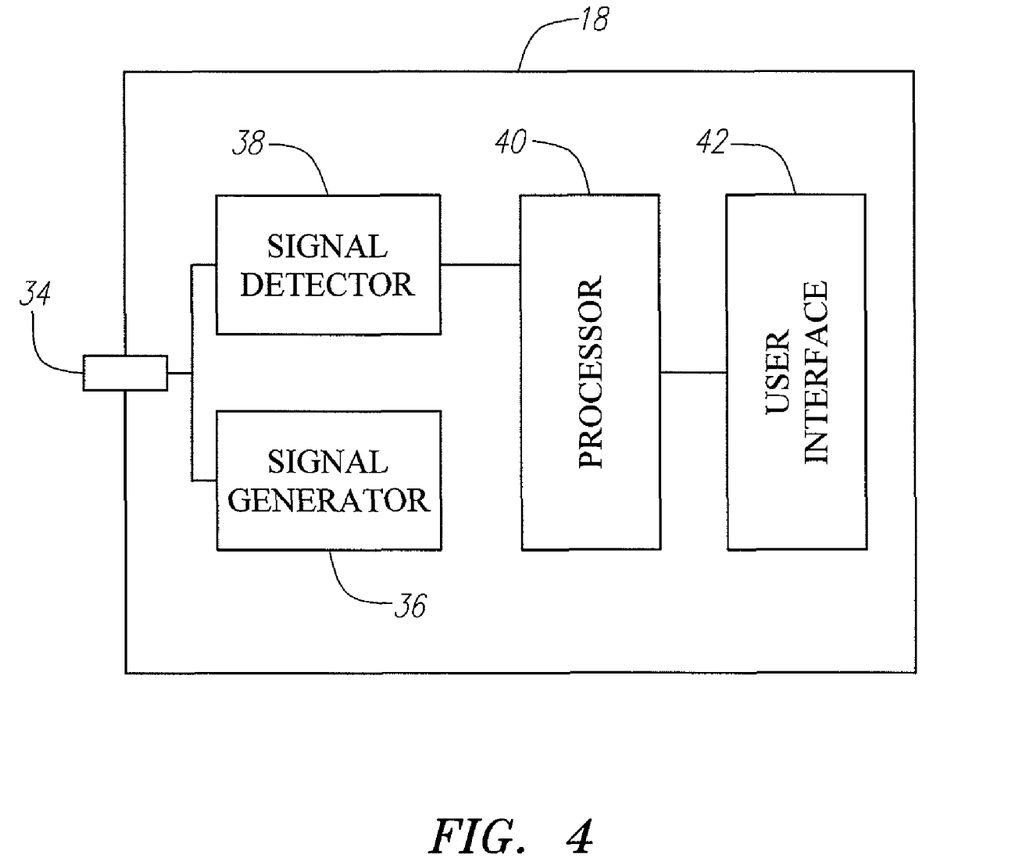
FIG. 4 is a block diagram of one embodiment of an electrode-tissue contact monitor used in the EP system of FIG. 1.

Referring now to FIGS. 1 and 4, the electrode-tissue contact monitor 18 utilizes the amplitude modulation concept illustrated in FIGS. 2 and 3A-3D to detect the occurrence and extent of contact between the tip electrode 24 of the mapping/ablation catheter 12 and heart tissue. To this end, the monitor 18 comprises an electrical terminal 34 to which the cable assembly 20 is mated, thereby coupling the catheter 12 (in particular, the electrodes 24, 26, 28) and ground patch electrode (not shown) to the monitor 18. The monitor 18 further comprises a signal generator 36 configured for transmitting a time varying signal (e.g., a sinusoidal wave having a frequency between 1 KHz to 100 KHz) between the tip electrode 24 and ground patch electrode (alternatively, the ring electrodes 26), and a signal detector 38 configured for sensing the magnitude of the voltage (if the signal generator 36 has a constant current source) or current (if the signal generator 36 has a constant voltage source) of the time varying signal. As discussed above, the electrical admittance between the tip electrode 24 and ground electrode, and thus, the voltage or current sensed by the signal detector 38, will be amplitude modulated by either the heart cycle or the respiratory cycle.

The monitor 18 comprises a processor 40 configured for detecting contact between the tip electrode 24 and tissue based on the amplitude modulation of sensed by the signal detector 38. In particular, the processor 40 compares the sensed magnitude of the amplitude modulation (i.e., the difference between the peak amplitude to the baseline amplitude) to a threshold level, and determines that the tip electrode 24 is in contact with the heart tissue if the magnitude of the amplitude modulation exceeds the threshold level, and determines that the tip electrode 24 is not in contact with the heart tissue otherwise.

If it is determined that the tip electrode 24 is in contact with the heart tissue, the processor 40 is configured for determining an extent of the electrode-tissue contact based on a magnitude of the sensed amplitude modulation. This can be accomplished, e.g., by accessing a look-up table containing amplitude modulation values and corresponding values indicative of the extent of contact. Such corresponding values can be, e.g., a position of the electrode relative to the undeflected surface of the heart tissue or a percentage of the area of the electrode covered by the heart tissue. The look-up table can, e.g., be generated based on empirical or modeled data. Alternatively, rather than using a look-up table, the extent of contact can be determined based on one or more closed-form equations, in which the magnitude of the amplitude modulation is input and out which the contact values are output. In an optional or alternative embodiment, the processor 40 may generate a warning signal indicating that contact between the tip electrode 24 and the heart tissue is dangerously close to the puncturing or otherwise inadvertently damaging the heart tissue. If a robotic system is used, the processor 40 may transmit a signal to the robotic system preventing further advancement of the catheter 12.

The monitor 18 further comprises a user interface 42 configured for conveying an output indicative of contact between the tip electrode 24 and the heart tissue. In particular, the user interface 42 includes a video monitor (not shown) configured to display the contact values determined by the processor 40. Alternatively, the user interface 42 may include a speaker (not shown) configured to audibly output the contact values. If the processor 40 generates a warning signal, the user interface 42 may also output the warning signal in the form of, e.g., a flashing icon on the video monitor or an audible sound from the speaker. In alternative embodiments, the user interface 42 simply outputs the amplitude modulation of the electrical admittance; that is, the measured electrical admittance over time. In this case, the processor 40 merely processes the magnitude of the voltage or current detected by the signal detector 38 for output as an electrical admittance to the user interface 42.

The occurrence and extent to which an electrode contacts heart tissue can also be determined based on a phase difference between the electrode and another electrode known to be not in contact with the heart tissue. In particular, a time-varying signal can be transmitted between the ring electrode 26 and ground, and then measured at the tip electrode 24 to form the circuit illustrated in FIG. 5.

Figure 5:
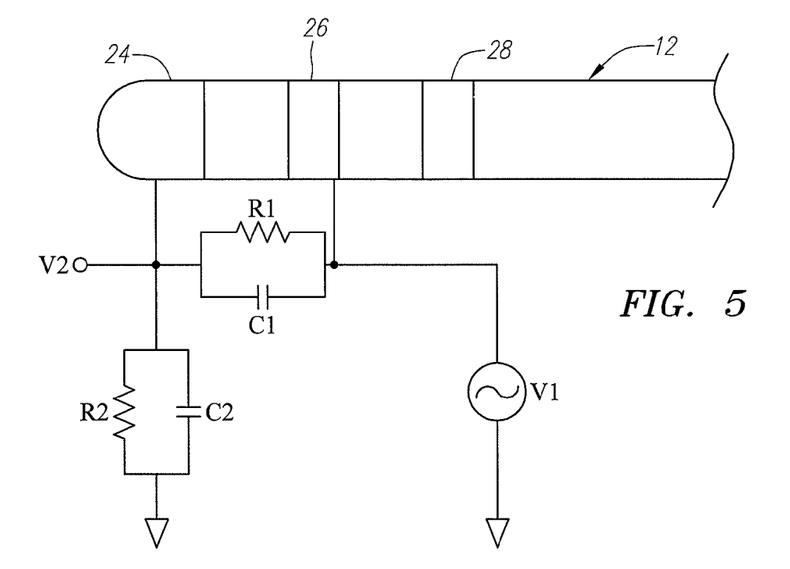
FIG. 5 is a side view of the distal end of the catheter used in the EP system of FIG. 1, particularly showing a circuit representation of the tissue/blood surrounding the catheter.

The circuit comprises a sinusoidal voltage source having a value V1 equal to the voltage of the time-varying signal supplied to the ring electrode 26, and a voltage V2 equal to the voltage of the time-varying signal measured by the tip electrode 24. Resistance R1 and capacitance C1 represent the impedance between the ring electrode 26 and the tip electrode 24, and resistance R2 and capacitance C2 represent the impedance between the tip electrode 24 and ground. Significantly, when both the tip electrode 24 and ring electrode 26 are immersed completely in blood (i.e., the tip electrode 24 is not in contact with heart tissue), the impedance between the ring electrode 26 and tip electrode 24 will be equal to the impedance between the tip electrode 24 and ground; that is $R1*C1=R2*C2$. Thus, there will be no phase shift between voltages V1 and V2; that is, no phase shift between the voltage generated at the ring electrode 26 and the voltage measured at the tip electrode 24. If, however, the tip electrode 24 is in contact with the tissue, which has a different complex permittivity than blood, the phase of voltage V2 will differ from voltage V1 as a function of frequency; that is, there will be a phase shift between the voltage generated at the ring electrode 26 and the voltage measured at the tip electrode 24. The phase difference between voltages V1 and V2 (i.e., the voltage generated at the ring electrode 26 and the voltage measured at the tip electrode 24) will increase as the contact between the tip electrode 24 and the tissue increases (i.e., as the area of the tip electrode 24 covered by the tissue increases).

In a similar manner, if the time-varying voltage is applied to the ring electrode 28, instead of the ring electrode 26, there will be no phase shift between the voltage generated at the ring electrode 28 and the voltage measured at the tip electrode 24 if the tip electrode 24 is not in contact with the tissue, while there will be a phase shift between voltage generated at the ring electrode 28 and the tip electrode 24 if the tip electrode 24 is in contact with the tissue, with the phase difference increasing as the contact between the tip electrode 24 and the tissue increases.

In this case, the time-varying voltage can also be measured at the ring electrode 26, as well as the tip electrode 24, to provide additional information. For example, if it is determined that the tip electrode 24 is not in contact with the tissue by virtue of detecting no phase difference between the voltage generated at the ring electrode 26 and the voltage measured at the tip electrode 24, the phase of the voltage measured at the ring electrode 28 can be compared to the phase of the voltage generated at the ring electrode 26 to confirm that the tip electrode 24 is, indeed, not in contact with the tissue; that is, no phase difference will confirm non-contact between the tip electrode 24 and tissue. In contrast, if it is determined that the tip electrode 24 is in contact with the tissue by virtue of detecting a phase difference between the voltage generated at the ring electrode 26 and the voltage measured at the tip electrode 24, the phase of the voltage measured at the electrode 28 can be compared to the phase of the voltage generated at the ring electrode 26 to confirm that the tip electrode 24 is, indeed, in contact with the tissue; that is, a phase difference will confirm contact between the tip electrode 24 and tissue.

Figure 6:
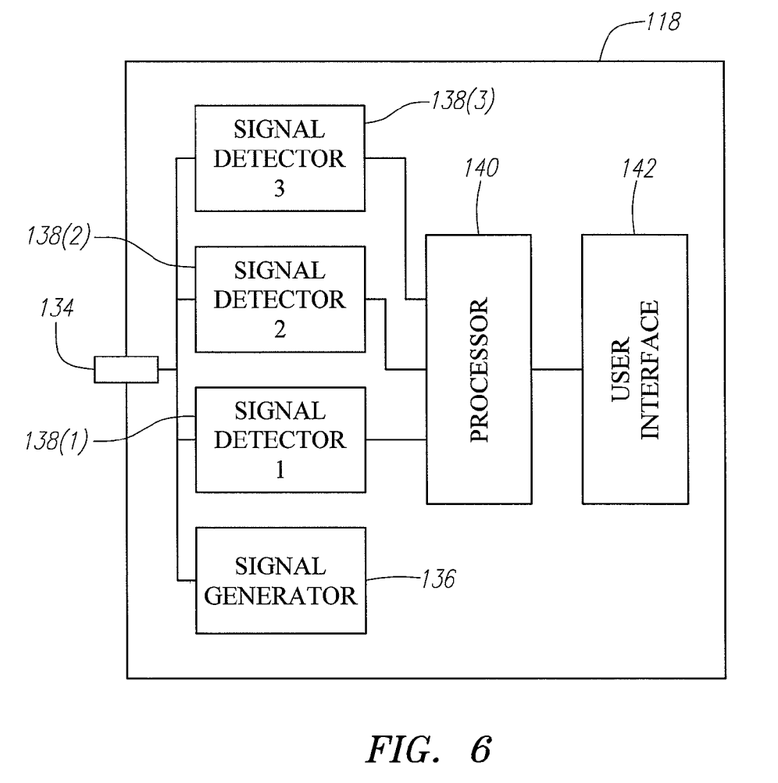
FIG. 6 is a block diagram of another embodiment of an electrode-tissue contact monitor used in the EP system of FIG. 1.

Referring to FIG. 6, an electrode-tissue contact monitor 118 utilizes the voltage phase difference concept illustrated in FIG. 5, as alternative to or in addition to the amplitude modulation concept, to detect the occurrence and extent of contact between the tip electrode 24 of the ablation/mapping catheter 12 and the heart tissue. To this end, the monitor 118 comprises an electrical terminal 134 to which the cable assembly 20 is mated, thereby coupling the catheter 12 (in particular, the electrodes 24, 26, 28) and ground patch electrode (not shown) to the monitor 118. The monitor 118 further comprises a signal generator 136 configured for transmitting a time varying signal (e.g., a sinusoidal wave having a frequency between 1 KHz to 100 KHz) between the ring electrode 26 (alternatively, the ring electrode 28) and the ground patch electrode, a first signal detector 138(1) configured for sensing the phase of the voltage of the time varying signal, and a second signal detector 138(2) configured for sensing the phase of the voltage of the time varying signal measured between the tip electrode 24 and the ground patch electrode. Optionally, the monitor 118 may comprise a third signal detector 138(3) configured for sensing the phase of the voltage of the time varying signal measured between the ring electrode 28 not supplied with the time varying signal and the ground patch electrode.

The monitor 18 comprises a processor 140 configured for detecting contact between the tip electrode 24 and tissue based on the voltage phases sensed by the first and second signal detectors 138(1) and 138(2). In particular, the processor 140 subtracts the voltage phase detected by the first signal detector 138(1) from the voltage phase sensed by the second signal detector 138(2) (or vice versa), and determines that the tip electrode 24 is in contact with the heart tissue if the magnitude of the phase difference exceeds a threshold level, and determines that the tip electrode 24 is not in contact with the heart tissue otherwise.

If the third signal detector 138(3) is provided as discussed above, the processor 140 may subtract the voltage phase sensed by the first signal detector 138(1) from the voltage phase sensed by the third signal detector 138(3)(or vice versa), and if the tip electrode 24 is determined to be contact with the tissue in the first instance, confirms this if the magnitude of the phase difference sensed by the first and third signal detectors 138(1), 138(3) exceeds a threshold level, and if the tip electrode 24 is determined to not be contact with the tissue in the first instance, confirms this if the magnitude of the phase difference sensed by the first and third signal detectors 138(1), 138(3) does not exceed the threshold level.

If it is determined that the tip electrode 24 is in contact with the tissue, the processor 140 is configured for determining an extent of the electrode-tissue contact based on a magnitude of the phase difference. This can be accomplished, e.g., by accessing a look-up table containing voltage phase difference values and corresponding values indicative of the extent of contact. Such corresponding values can be, e.g., a position of the electrode relative to the undeflected surface of the tissue or a percentage of the area of the electrode covered by the tissue. The look-up table can, e.g., be generated based on empirical or modeled data. Alternatively, rather than using a look-up table, the extent of contact can be determined based on one or more closed-form equations, in which the magnitude of the phase difference is input and out which the contact values are output. In an optional or alternative embodiment, the processor 140 may generate a warning signal indicating that contact between the tip electrode 24 and the tissue is dangerously close to the puncturing or otherwise inadvertently damaging the tissue.

The monitor 118 further comprises a user interface 142 configured for conveying an output indicative of contact between the tip electrode 24 and the tissue. In particular, the user interface 42 includes a video monitor (not shown) configured to display the contact values determined by the processor 40. Alternatively, the user interface 142 may include a speaker (not shown) configured to audibly output the contact values. If the processor 140 generates a warning signal, the user interface 42 may also output the warning signal in the form of, e.g., an flashing icon on the monitor 118 or an audible sound from the speaker. In alternative embodiments, the user interface 142 simply outputs the phase difference. In this case, the processor 140 merely processes the phase difference for output to the user interface 142. If a robotic system is used, the processor 140 may transmit a signal to the robotic system preventing further advancement of the catheter 12.

It should be appreciated that, while the force between the electrode and heart tissue cannot be determined directly by measuring the modulation of the admittance or the voltage phase difference using the techniques described above, the extent to which the heart tissue wraps around the electrode can be determined, which may actually be more useful than determining force, since the heart walls of different patients will puncture at different applied forces. For example, given the same applied force, a thin heart wall, which may typically be found in older patients, will puncture before a thicker heart wall. However, because the thinner heart wall will wrap around an electrode more than a thicker heart wall given the same applied force, the measured contact admittance will be greater with respect to the thinner heart wall than the thicker heart wall, thereby providing a more reliable means for preventing puncture, as well as a more reliable means for indicating the occurrence of tissue tenting when desired. In addition, depth of electrode insertion into heart tissue is a better indication of electrode-tissue contact sufficient for ablation than is applied force.

Figure 7A:
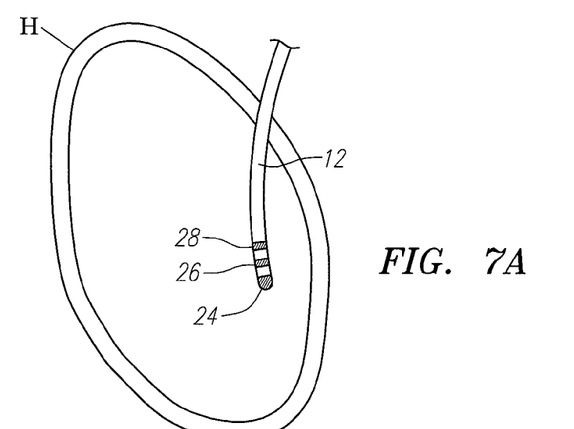
FIGS. 7A-7C are side views illustrating a method of using the EP system of FIG. 1 to map and ablate aberrant regions in a heart.

Having described the structure of the EP system 10, one method of using it to locate and treat an aberrant conductive pathway within the heart H, such as those typically associated with ventricular tachycardia or atrial fibrillation, will now be described. First, under fluoroscopy, the mapping/ablation catheter 12 is intravenously introduced into the appropriate chamber of the heart H, into the appropriate chamber of the heart H (FIG. 7A). For example, if the disease to be treated is ventricular tachycardia, the catheter 12 will be introduced into the left ventricle. If the disease to be treated is atrial fibrillation, the catheter 12 will be introduced into the left atrium. During this time period, the electrode-tissue contact monitor 18 (or alternatively, monitor 118) may be operated to determine the extent of contact between the tip electrode 24 and the heart tissue. This may especially be useful if the catheter 12 is being manipulated by a robotic system.

Figure 7B:
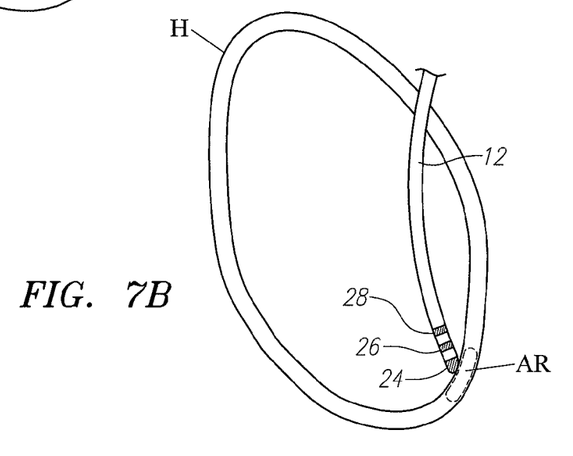
Figure 7C:
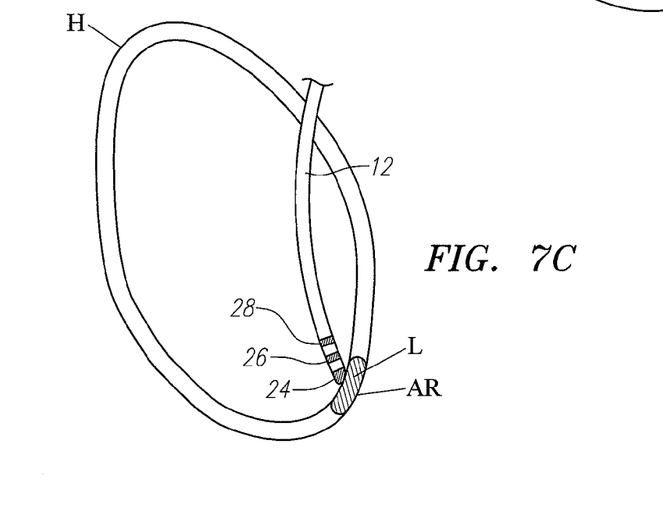

The catheter 12 is then moved around within the selected chamber of the heart H as the mapping processor 14 is operated to record electrical activity within the heart 10 and derive mapping data therefrom. If an aberrant region AR identified, the tip electrode 24 of the mapping/ablation catheter 12 is placed into contact with the aberrant region AR (FIG. 7B). During this time period, the electrode-tissue contact monitor 18 (or alternatively, monitor 118) may again be operated to determine the occurrence and extent of contact between the tip electrode 24 and the heart tissue. When proper and firm contact between the tip electrode 24 and the heart tissue has been determined, the RF generator 36 is then operated to therapeutically create a lesion L at the aberrant region AR (FIG. 7C). During the ablation process, the electrode-tissue contact monitor 18 (or alternatively, the monitor 118) may be operated to ensure that proper and firm contact between the tip electrode 24 and the heart tissue is maintained. After the ablation process is complete, the mapping processor 14 can again be operated to ensure that the heart disease has been successfully treated. If additional aberrant conductive pathways have been found, the ablation step can be repeated. If no aberrant conductive pathways have been found, the catheter 12 can then be removed from the patient.

Although particular embodiments of the present invention have been shown and described, it will be understood that it is not intended to limit the present invention to the preferred embodiments, and it will be obvious to those skilled in the art that various changes and modifications may be made without departing from the spirit and scope of the present invention. Thus, the present inventions are intended to cover alternatives, modifications, and equivalents, which may be included within the spirit and scope of the present invention as defined by the claims.

What is claimed is:

1. A medical system, comprising:
   a medical probe having a probe shaft and a first electrode carried by the probe shaft;
   a second electrode; and
   a tissue contact monitoring device configured for measuring an electrical parameter between the first electrode and the second electrode, wherein the electrical parameter is amplitude modulated by a physiological cycle of a patient, and for detecting whether a signal of the amplitude modulation of the electrical parameter has substantially the same directionality at least temporarily as a measured signal of the physiological cycle of the patient to provide an output indicative of contact between the medical probe and a tissue; and conveying the output to a user.

2. The system of claim 1, wherein the medical probe is an intravascular catheter.

3. The system of claim 1, wherein the first electrode is a tip electrode.

4. The system of claim 1, wherein the second electrode is a ground patch electrode configured for being attached to the skin of the patient.

5. The system of claim 1, wherein the second electrode is carried by the probe shaft.

6. The system of claim 1, wherein the electrical parameter is an electrical admittance.

7. The system of claim 1, wherein the monitoring device is configured for transmitting a time varying signal between the first electrode and the second electrode, and detecting the time varying signal, wherein the electrical parameter measurement is based on the detection of the time varying signal.

8. The system of claim 1, wherein the physiological cycle is a respiratory cycle.

9. The system of claim 1, wherein the physiological cycle is a cardiac cycle.

10. The system of claim 1, wherein the monitoring device is configured for comparing a magnitude of the amplitude modulation to a threshold, and determining that the medical probe is in contact with the tissue if the magnitude of the amplitude modulation exceeds the threshold.

11. The system of claim 1, wherein the monitoring device is configured for determining an extent of the contact based on a magnitude of the amplitude modulation.

12. The system of claim 1, wherein the detected contact is between the first electrode and the tissue.

13. The system of claim 1, wherein the output is a visual display of the amplitude modulation of the measured electrical parameter.

14. The system of claim 1, further comprising a radio frequency (RF) generator configured for delivering ablation energy to the first electrode.

15. The medical system of claim 1, wherein the tissue contact monitoring device is configured for measuring an electrical parameter at a constant frequency over time.

16. A tissue contact monitoring device, comprising:
- an electrical terminal configured for coupling to a medical probe having a first electrode; and
- a processor configured for measuring an electrical parameter between the first electrode and a second electrode, wherein the electrical parameter is amplitude modulated by a physiological cycle of a patient, and detecting whether a signal of the amplitude modulation of the electrical parameter has substantially the same directionality at least temporarily as a measured signal of the physiological cycle of the patient to provide an output indicative of contact between the medical probe and a tissue; and
- a user interface configured for conveying an output indicative of contact between the medical probe and a tissue.

17. The monitoring device of claim 16, wherein the electrical parameter is an electrical admittance.

18. The monitoring device of claim 16, wherein the physiological cycle is a respiratory cycle.

19. The monitoring device of claim 16, wherein the physiological cycle is a cardiac cycle.

20. The monitoring device of claim 16, wherein the processor is configured for comparing a magnitude of the amplitude modulation to a threshold, and determining that the medical probe is in contact with the tissue if the magnitude of the amplitude modulation exceeds the threshold.

21. The monitoring device of claim 16, wherein the processor is configured for determining an extent of the contact based on a magnitude of the amplitude modulation.

22. The monitoring device of claim 16, further comprising:
- a signal generator configured for transmitting a time varying signal between the first electrode and the second electrode; and
- a signal detector configured for detecting the time varying signal, wherein the processor is configured for measuring the electrical parameter based on the detected time varying signal.

23. The monitoring device of claim 16, wherein the user interface comprises a video monitor, and the output is a visual display of the amplitude modulation of the measured electrical parameter.

* * * * *